US00PP12365P2

(12) United States Plant Patent
Utecht

(10) Patent No.: US PP12,365 P2
(45) Date of Patent: Jan. 22, 2002

(54) GERANIUM PLANT NAMED 'FISROCKY ORANGE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/631,660

(22) Filed: Aug. 3, 2000

(51) Int. Cl.[7] ..... A01H 5/00
(52) U.S. Cl. ..... Plt./327
(58) Field of Search ..... Plt./327, 328

(56) References Cited

U.S. PATENT DOCUMENTS

PP5,757 P * 7/1986 Buck ..... Plt./327

OTHER PUBLICATIONS

Fischer Selections 1999/2000 Catalogue offering 'Tango Orange' ('Fisrocky Orange') on p. 9.
Swiss Application for 'Fisrocky Orange' (Apr. 22, 1999).
European Union Application for 'Fisrocky Orange' (Aug. 17, 1998).
European Union Grant for 'Fisrocky Orange' (Aug. 16, 1999).
German Application for 'Fisrocky Orange' (Aug. 17, 1998).
German Grant for 'Fisrocky Orange' (Jan. 15, 1999).
Canadian Application, Denomination, Plant Varieties Journal No. 33, Oct. 1999 Canada.
GTITM UPOVROM citation for 'Fisrocky Orange' as per QZ PBR 980697; May 12, 1998.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrocky Orange', as described and illustrated, and particularly characterized by the combined features of orange, semi-double flowers, rich flowering, dark-green foliage with distinct zonation, medium to strong growth habit forming wide but not very tall plants, and relatively early flowering response.

1 Drawing Sheet

BACKGROUND OF THE INVENTION

The present invention relates to a new and distinct cultivar of geranium plant, botanically known as *Pelargonium zonale*, and hereinafter referred to by the cultivar name 'Fisrocky Orange'.

'Fisrocky Orange' is a product of a planned breeding program which had the objective of creating new geranium varieties with orange to intense salmon flower color in combination with dark-green foliage.

'Fisrocky Orange' originated from a hybridization made by the inventor, Angelika Utecht, in a controlled breeding program in Galdar, Gran Canaria, Spain, in 1992. The female parent was a hybrid seedling, designated no. 1020-6 (unpatented), having salmon-pink, semi-double flowers, dark-green foliage with very weak zonation, and compact plant habit. The male parent was the commercial variety 'Najda' (unpatented), which is characterized by orange flower color, early flowering response, medium-green foliage with strong zonation, and relatively compact plant habit.

'Fisrocky Orange' was selected as one flowering plant within the progeny of the stated cross by the inventor, Angelika Utecht, in 1993 in a controlled environment in Galdar, Gran Canaria, Spain.

The first act of asexual reproduction of 'Fisrocky Orange' was accomplished when vegetative cuttings were taken from the initial selection in the fall of 1993 in a controlled environment in Galdar, Gran Canaria, Spain, by, or under the supervision of, Angelika Utecht. Horticultural examinations of plants grown from cuttings of the plant, initiated in May 1995 in Hillscheid, Germany, and continuing thereafter, has demonstrated that the combination of characteristics as herein disclosed for 'Fisrocky Orange' are firmly fixed and are retained through successive generations of asexual reproduction.

BRIEF DESCRIPTION OF THE INVENTION

The following traits have been repeatedly observed and are determined to be basic characteristics of 'Fisrocky Orange', which in combination distinguish this geranium as a new and distinct cultivar:

1. semi-double, orange flowers;
2. large inflorescences borne well-above the foliage;
3. dark-green foliage with distinct zonation;
4. medium to strong growth, and a rather wide, but not very tall (high) foliage canopy; and
5. early to medium spring flowering response.

'Fisrocky Orange' has not been observed under all possible environmental conditions. The phenotype of the new cultivar may vary significantly with variations in environment such as temperature, light intensity and day length without any change in the genotype. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fisrocky Orange' are the parental variety 'Nadja' and the varieties 'Fischampion' (U.S. Plant Pat. No. 9,400), 'Fismega' (U.S. Plant Pat. No. 9,773), and 'Fisglori' (U.S. Plant patent application Ser. No. 09/323,150, abandoned). In comparison to 'Fischampion', 'Fisrocky Orange' has a lighter-orange tone of flower color and larger inflorescences on stronger, usually green-colored peduncles, while 'Fischampion' has thin and partly dark-red peduncles.

In contrast to 'Fismega', which has single-type flowers, 'Fisrocky Orange' has semi-double flowers of a slightly different color and a somewhat stronger zonation of leaves. Furthermore, the peduncles of 'Fismega' have a distinctly stronger, reddish coloration than the peduncles of 'Fisrocky Orange'.

In comparison to 'Fisglori', 'Fisrocky Orange' has a lighter-orange, instead of orange-red, flower color and dark-green foliage with stronger zonation, while 'Fisglori' has medium-green leaves with weak zonation. Furthermore, the plant habit of 'Fisrocky Orange' is normally wider than the more round plants of 'Fisglori'.

In comparison to 'Nadja', which has medium-green foliage, 'Fisrocky Orange' has dark-green leaves with narrower and weaker zonation, larger inflorescences, and more vigorous growth.

BRIEF DESCRIPTION OF THE DRAWING

The accompanying photographic illustration shows typical flower and foliage characteristics of 'Fisrocky Orange' with colors being as true as possible with an illustration of this type.

DETAILED BOTANICAL DESCRIPTION

The measurements were taken in Langley, British Columbia, Canada, On Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

Classification:

*Botanical.*—A hybrid of the species *Pelargonium zonale L'Hérit.*

*Commercial.*—Zonal geranium, cv. 'Fisrocky Orange'.

Inflorescence:

*Type.*—Umbel. Shape: Almost semi-spherical. Average diameter: 94 mm. Average depth: 50 mm. Peduncle length: 152 mm. Peduncle color: Light-green, variable between RHS 143 B and RHS 143 C; no anthocyanin. Pedicel length: 35 mm. Pedicel color: Green, RHS 143 B, slight infusion of anthocyanin may occur near the upper end, brownish RHS 179 B. Number of flowers per umbel: About 20–25. Lastingness of the umbel: About 18 days at 18° C.

*Corolla.*—Average diameter: 53 mm. Form: Semi-double. Shape: Zygomorph, with a gap on each side separating the upper petals from the lower petals. Number of petals: 7.9. Size of petals: Upper petals are approximately 30–31 mm long, 21–23 mm wide, lower petals are approximately 25–27 mm in both length and width. Shape of petals: Obovate, attenuate base, upper end rounded, margin entire. Color (general tonality from a distance of three meters): Orange. Color of upper petals: RHS 40 B. Markings of upper petals: Slight pinkish coloring at the base, RHS 48 B. Color of lower petals: From RHS 41 B to RHS 41 C. Color of lower surface of petals: Mainly RHS 40 B. Number of petaloids: 1–3. Color of petaloids: Upper surface near RHS 40 B, lower surface RHS 41 C. Color of sepals: Outer surface green, RHS 143 B, inner surface light-green, RHS 143 C. Number of sepals: 5. Size of sepals: 11–12 mm in length, 4 mm wide for the largest, upper sepal, 2–3 mm wide for other sepals. Sepal Shape: Linear to lanceolate, acute tip, truncate base, entire margin, weak short pubescence texture.

*Bud (just before petals unfold).*—Shape: Elliptical. Color (sepals): Green, RHS 143 B. Color (petals): Orange, variable from RHS 40 B to RHS 41 B. Length: 19 mm. Width: 9 mm.

*Reproductive organs.*—Androecium: Most often 3–5 fertile anthers, white filaments and orange pollen, RHS 30 A, moderate pollen production. Gynoecium: 5–6 lobed stigma, light orange, whitish filament, one pistil per flower. Fertility/seed set: Occasionally, a few seeds are developed, oblong, 4–5 mm, brown RHS 177 B.

*Spring flowering response period.*—In Hillscheid, Germany, in 1999, plants had on average 1.6 flowers opened 9 weeks after planting of unrooted cuttings.

*Outdoor flower production.*—Rich flowering; the flower count in 1999, in Hillscheid, Germany, indicated about 4.25 inflorescences per plant in mid-May.

*Durability.*—Good stability of flower color with very little fading and relatively good rain resistance.

*Lastingness of the individual bloom.*—9 days at 18° C.

*Fragrance.*—None.

Plant:

*Foliage.*—Shape: Kidney-shape, with open, cordate base, rounded with very weak lobes. Margin: Bicrenated, relatively strong crenation. Size of leaf: 77 mm wide, 48–53 mm long. Color of upper surface: Dark-green, from RHS 137 A to RHS 137 B. Color of zonation: Dark-brown, about RHS 166 A, forming a relatively narrow ring, medium strong in spring, may fade somewhat during the summer. Petioles: 55–65 mm long, 3 mm in diameter, color approximately RHS 143 C.

*General appearance and form.*—Internode length: 30–40 mm. Branching pattern: 6.8 branches. Plant size: 18.2 cm high as measured from the base of the stem (soil surface) to the surface of the foliage canopy, without the inflorescences; 32.9 cm wide.

Disease/pest resistance/susceptibility: None observed to date.

I claim:

1. A new and distinct cultivar of geranium plant named 'Fisrocky Orange', as described and illustrated.

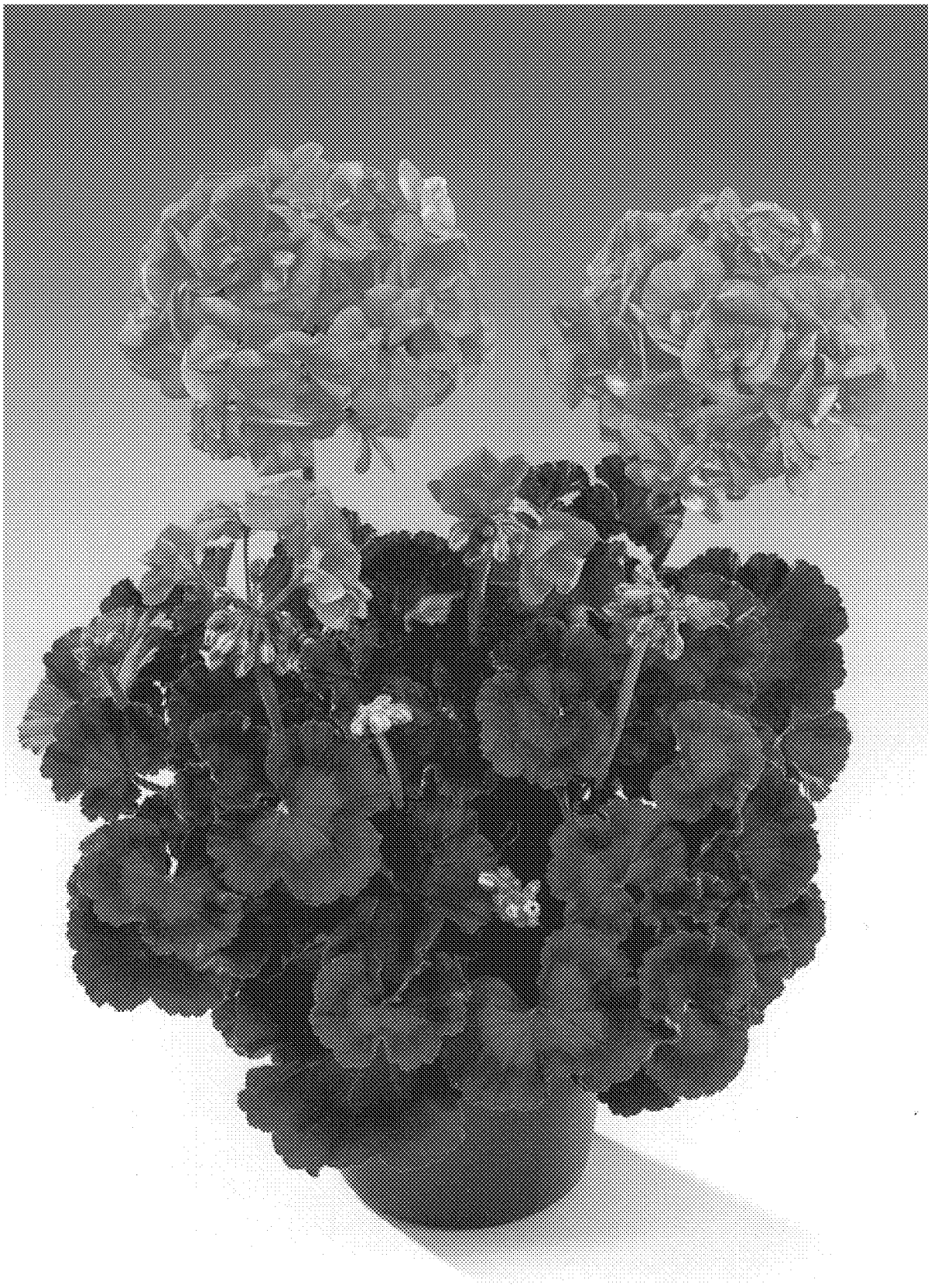

* * * * *